(12) United States Patent
Hölljes

(10) Patent No.: US 8,123,527 B2
(45) Date of Patent: Feb. 28, 2012

(54) ACTIVE LEARNING DEVICE AND METHOD

(76) Inventor: H. Christian Hölljes, San Rafael, CA (US)

( * ) Notice: Subject to any disclaimer, the term of this patent is extended or adjusted under 35 U.S.C. 154(b) by 1079 days.

(21) Appl. No.: 11/757,184

(22) Filed: Jun. 1, 2007

(65) Prior Publication Data

US 2008/0102424 A1    May 1, 2008

Related U.S. Application Data

(60) Provisional application No. 60/855,578, filed on Oct. 31, 2006.

(51) Int. Cl.
*G09B 9/02* (2006.01)
*A63B 21/00* (2006.01)

(52) U.S. Cl. ............... 434/29; 434/30; 434/61; 434/62; 434/156; 434/159; 434/167; 434/176; 434/191; 434/57; 434/247; 482/4; 482/8; 482/9; 482/51; 463/9; 463/36

(58) Field of Classification Search .............. 434/29, 434/30, 61, 62, 57, 156, 159, 167, 176, 191, 434/247; 463/9, 36; 482/4, 8, 9, 51
See application file for complete search history.

(56) References Cited

U.S. PATENT DOCUMENTS 3,834,702 A    9/1974   Bliss
4,121,488 A    10/1978  Akiyama
(Continued)

OTHER PUBLICATIONS

Charles I. Kelly, "Catch the Spelling", http://www.manythings.org/cts/sc999.htm, Copyright (C) 2004, pp. 1-13.*

*Primary Examiner* — Xuan Thai
*Assistant Examiner* — Jack Yip
(74) *Attorney, Agent, or Firm* — Patent Law Offices of Michael E. Woods; Michael E. Woods

(57) ABSTRACT

An activity device including an activity sensor generating an activity interaction signal responsive to a sustained large-muscle physical activity of a user operating the activity device; a controller, coupled to the activity monitor, generating a virtual environment supporting a virtual user frame-of-reference in the virtual environment, the controller generating a set of virtual education elements in the environment and a goal for the set virtual representation with respect to the virtual education elements wherein the controller is responsive to the activity interaction signal to produce an affected interaction of the virtual representation with the virtual education elements with the controller measuring a conformation of the goal by the affected interaction; and a feedback system, coupled to the controller, presenting the virtual environment with the frame-of-reference in relation to the virtual education elements providing the user with feedback regarding the goal and the conformation of the goal by the affected interaction.

2 Claims, 16 Drawing Sheets

U.S. PATENT DOCUMENTS

| | | | |
|---|---|---|---|
| 4,491,050 A | 1/1985 | Franzmann | |
| 4,512,567 A | 4/1985 | Phillips | |
| 4,542,897 A * | 9/1985 | Melton et al. | 463/7 |
| 4,813,665 A | 3/1989 | Carr | |
| 4,940,234 A | 7/1990 | Ishida et al. | |
| 5,139,261 A | 8/1992 | Openiano | |
| 5,142,358 A * | 8/1992 | Jason | 348/61 |
| 5,219,291 A | 6/1993 | Fong et al. | |
| 5,240,417 A | 8/1993 | Smithson et al. | |
| 5,415,549 A | 5/1995 | Logg | |
| 5,462,503 A | 10/1995 | Benjamin et al. | |
| 5,591,104 A | 1/1997 | Andrus et al. | |
| 5,645,513 A * | 7/1997 | Haydocy et al. | 482/57 |
| 5,839,976 A | 11/1998 | Darr | |
| 5,839,990 A | 11/1998 | Virkkala | |
| 5,855,483 A * | 1/1999 | Collins et al. | 434/322 |
| 5,888,172 A * | 3/1999 | Andrus et al. | 482/7 |
| 5,890,995 A * | 4/1999 | Bobick et al. | 482/4 |
| 5,971,761 A | 10/1999 | Tillman, Sr. | |
| 5,971,855 A | 10/1999 | Ng | |
| 5,993,216 A | 11/1999 | Stogner | |
| 5,997,304 A | 12/1999 | Wood | |
| 6,004,243 A | 12/1999 | Ewert | |
| 6,024,675 A | 2/2000 | Kashiwaguchi | |
| 6,083,106 A | 7/2000 | McDowell | |
| 6,106,297 A | 8/2000 | Pollak et al. | |
| 6,126,571 A | 10/2000 | Parks | |
| 6,142,877 A | 11/2000 | Nishimura | |
| 6,142,913 A | 11/2000 | Ewert | |
| 6,152,856 A | 11/2000 | Studor et al. | |
| 6,213,872 B1 * | 4/2001 | Harada et al. | 463/7 |
| 6,217,449 B1 | 4/2001 | Kaku | |
| 6,244,988 B1 * | 6/2001 | Delman | 482/8 |
| 6,261,101 B1 * | 7/2001 | Benitz et al. | 434/167 |
| 6,293,798 B1 | 9/2001 | Boyle et al. | |
| 6,302,789 B2 * | 10/2001 | Harada et al. | 463/7 |
| 6,336,891 B1 | 1/2002 | Fedrigon et al. | |
| 6,447,424 B1 | 9/2002 | Ashby et al. | |
| 6,530,864 B1 | 3/2003 | Parks | |
| 6,669,562 B1 * | 12/2003 | Shiino | 463/31 |
| 6,743,971 B1 | 6/2004 | Chen | |
| 6,755,657 B1 * | 6/2004 | Wasowicz | 434/167 |
| 6,805,604 B2 | 10/2004 | Brumagin et al. | |
| 6,808,267 B2 * | 10/2004 | O'Neil et al. | 351/246 |
| 6,881,176 B2 * | 4/2005 | Oishi et al. | 482/8 |
| 7,022,048 B1 * | 4/2006 | Fernandez et al. | 482/8 |
| 7,044,891 B1 * | 5/2006 | Rivera | 482/8 |
| 7,090,619 B2 | 8/2006 | Miyamaru et al. | |
| 7,128,649 B2 | 10/2006 | Nobe et al. | |
| 7,246,050 B2 | 7/2007 | Sheridan | |
| 7,699,755 B2 * | 4/2010 | Feldman et al. | 482/8 |
| 7,811,200 B2 * | 10/2010 | Chiang | 482/1 |
| 2002/0055383 A1 | 5/2002 | Onda et al. | |
| 2003/0017913 A1 * | 1/2003 | Stewart | 482/8 |
| 2003/0077556 A1 | 4/2003 | French et al. | |
| 2003/0078138 A1 * | 4/2003 | Toyama | 482/8 |
| 2003/0099919 A1 | 5/2003 | Love | |
| 2003/0134714 A1 * | 7/2003 | Oishi et al. | 482/6 |
| 2004/0076942 A1 * | 4/2004 | O'Neil et al. | 434/350 |
| 2005/0130741 A1 * | 6/2005 | Pandian | 463/36 |
| 2005/0164601 A1 * | 7/2005 | McEachen et al. | 446/456 |
| 2005/0209066 A1 * | 9/2005 | Penney | 482/84 |
| 2006/0030385 A1 * | 2/2006 | Barney et al. | 463/9 |
| 2006/0054679 A1 | 3/2006 | Ruping | 235/375 |
| 2006/0217243 A1 * | 9/2006 | Feldman et al. | 482/91 |
| 2006/0229163 A1 * | 10/2006 | Waters | 482/8 |
| 2006/0246975 A1 * | 11/2006 | Pellegrini et al. | 463/10 |
| 2007/0003913 A1 * | 1/2007 | Rosenberg | 434/156 |
| 2007/0008089 A1 * | 1/2007 | Ichimi et al. | 340/432 |
| 2007/0219050 A1 * | 9/2007 | Merril | 482/1 |
| 2007/0238079 A1 * | 10/2007 | Harrison | 434/236 |
| 2008/0070682 A1 * | 3/2008 | Woody | 463/30 |

* cited by examiner

ACTIVE LEARNING DEVICE AND METHOD

CROSS REFERENCE TO RELATED APPLICATIONS

This Application claims the benefit of U.S. Provisional Application 60/855,578 filed on 31 Oct. 2006, the contents of which are hereby expressly incorporated by reference in its entirety for all purposes.

BACKGROUND OF THE INVENTION

The present invention relates generally to education and more specifically to active learning having a user immersed in a virtual environment that supports a user reference that is interactive with educational elements and having sustained large muscle activity.

Interactive devices are well-known. There are systems and methods for linking various types of user activity with a display image. For example, a video game offers various personal perspectives (e.g., first-person or third-person views) of a representation of the user recreated within the game space. Typically the user uses a hand-operated interface device (keyboard, keypad, and/or joystick) to move the representation of the user within the game space and perform various desired in-game activities. The video game typically does not offer educational elements reinforced through the user/representation interaction. Additionally, the user typically is using small muscles of the hands and fingers for non-sustained (burst) quick, deft, accurate control of the representation.

There are other systems and methods known in the art. These include golf-training aids and exercise equipment. A golf-training aid includes a sensor to detect how a user has swung a club and to reproduce either a representation of that swing and/or to generate a simulation of results of that swing. The exercise equipment includes stationary bicycles that provide a relief for some concerning some monotony experienced by some users. The relief is provided by including a scrolling background, sometimes linked to a calculated bike speed for the user. A similar use is employed for rowing machines.

Studies have begun to show a positive connection between learning and oxygenated state for the learner. While reading a book while sustained use of certain exercise equipment may help "learn" content from the book, the learning is not interactive with the activity and the opportunity for multimedia and immersion (and thus enhanced learning of additional content is lost).

What is needed is a system and method for interactive, sustained, and immersive learning in a virtual environment having a user-controllable self-reference frame while in an active aerobic state.

BRIEF SUMMARY OF THE INVENTION

The present invention provides a system and method for interactive, sustained, and immersive learning in a virtual environment having a user-controllable self-reference frame while in an active and therefore an oxygenated state. ActiveLearning embodiments relate to methods and apparatus for delivering information, concepts, and instruction, particularly to children though some systems and methods are adaptable for older users. Preferred embodiments include implications of electronic implementation (for example, software supporting an electronic interface-device) which is a shorthand for "Active Electronic Learning." Some embodiments include a plurality of active interface devices or what are sometimes herein referred to as a kinetic-interactive-device (K.I.D.) which is: an apparatus or implement(s) that a user physically interacts with while responding to associated software-generated visual and/or audio cues that result from and correlate to the user's physical actions. The ActiveLearning methodology contends that information, concepts, and instruction delivered to the user, in conjunction with at least one or more periods of sustained physical movement (e.g. pedaling, stepping, running in place, turning handlebars, and/or moving their hands as in waving or punching) via a dynamic "activity toy," are absorbed and retained more quickly and effectively than when the user is passive or stationary. Consequently, embodiments of the invention(s) described herein are designed specifically to engage users intellectually and keep their bodies physically moving as they interact with a kinetic-interactive-device (K.I.D.) and multimedia systems/software which increase focus and the absorption and retention of information. (A user's physical activity while playing on a kinetic-interactive-device (K.I.D.) may include sustained large muscle movement as well as large muscle movement punctuated by resting pauses and small muscle activities.)

More particularly, embodiments of the present invention are related to a user-ergonomic, electronic, smart, kinetic-interactive-device or apparatus or method which either plugs into audio video equipment such as a computer, TV, home entertainment system, or network and/or connects wirelessly to certain ones of the devices, or has this audio video equipment/technology embedded or incorporated into the active-play/learn apparatus, device, or implement.

ActiveLearning methodology and kinetic-interactive-device (K.I.D.) apparatus are based on groundbreaking research that indicates that movement and exercise facilitate learning by producing oxygenated muscles and brain tissue, promoting neuron growth and circuits in the centers of memory and learning in the brain, and stimulating other brain neurotransmitters, thereby increasing awareness, focus, and memory capacity. The ActiveLearning methodology engages the whole user, body and mind, as they produce large and small musculoskeletal movement in thoughtful response to visual and audio cues, instructions as well as tactile or olfactory feedback. This learning methodology also mimics the fundamental immersive quality of play by combining physical activity, the delivery of information and concepts correlated to physical actions, and the power of imagination. Some key demonstrable benefits of the ActiveLearning methodology and variety of kinetic-interactive-devices (K.I.D.s) apparatus are (but are not limited to):

Increased absorption and retention of information due to: Neurogenesis;
Enhanced physiological receptivity;
Multi-sensory input and feedback;
Heightened levels of immersive, experiential learning and play;
Safe, comfortable, ergonomic apparatus; and
Collaborative ActiveLearning (locally or via a plurality of networks).

FIG. 1 is a perspective view of a set of representative preferred embodiments of the present invention (which may be implemented as wireless or wireless connections). From left to right the embodiments include: a jump-to-learn system, a climb-to-learn system, a scoot-to-learn system, a step-to-learn system (having either an interactive mat to detect step position, interactive appendage sensors attached to wrists/ankles of a user to detect movement or combination thereof), a punch-to-learn system, and a row-to-learn system. Of course, other activities are possible and include, for example, running, stepping, jumping, pedaling, steering, scooting, pushing, dancing, hopping, boxing, dodging, rowing, climbing, kicking, punching, pulling, and sliding.

A further advantage of certain embodiments of the present invention, the ActiveLearning method, while primarily a learning method, is also a "Trojan Horse" for increasing exercise, thereby also addressing increases in obesity and rise of Type 2 Diabetes in children or other young adults or users.

Disclosed is an apparatus and method for an immersive active educational invention. A preferred embodiment of the apparatus includes an activity device including an activity sensor for generating an activity interaction signal responsive to a sustained large-muscle physical activity of a user operating the activity device; a controller, coupled to the activity monitor, generating a virtual environment supporting a virtual user frame-of-reference in the virtual environment, the controller generating a set of virtual education elements in the environment and a goal for the set virtual representation with respect to the virtual education elements wherein the controller is responsive to the activity interaction signal to produce an affected interaction of the virtual representation with the virtual education elements with the controller measuring a conformation of the goal by the affected interaction; and a feedback system, coupled to the controller, for presenting the virtual environment with the frame-of-reference in relation to the virtual education elements for providing the user with feedback regarding the goal and the conformation of the goal by the affected interaction.

The method includes a) operating a kinetic interactive device to generate an activity interaction signal responsive to a sustained large-muscle physical activity of a user; b) generating, responsive to operation of the kinetic interactive device, a virtual environment supporting a frame-of-reference, the controller generating a set of virtual education elements in the environment and a goal for the frame-of-reference with respect to the virtual education elements wherein the generating is responsive to the activity interaction signal to produce an affected interaction of the frame-of-reference with the virtual education elements with the controller measuring a conformation of the goal by the affected interaction; and c) producing feedback data of the virtual environment with the frame-of-reference in relation to the virtual education elements that provide the user with information regarding the goal and the conformation of the goal by the affected interaction.

The foregoing summary, as well as the following detailed descriptions of preferred embodiments of the invention and manifestations of the learning method, will be better understood when read in conjunction with the associated drawings. For the purpose of illustrating the invention, there are shown in the drawings embodiments and software descriptions which are presently preferred. It should be understood, however, that the invention is not limited to the precise arrangements and instrumentalities shown.

Embodiments of the invention include an instructional delivery method hereupon named ActiveLearning, which is based on a plurality of specially designed K.I.D.s and associative software. The ActiveLearning instructional delivery method is based on real-time interactivity and coordination between the user's physical input to the K.I.D. and multimedia software specially designed to create a correspondence between physical input and access to and manipulation of intellectual or academic information, concepts, and instruction, and instructional and other events such as for example, operation or manipulation of a user reference generated in the environment controlled by user actions/activities.

As part of the ActiveLearning instructional delivery method, the specific technologies that are built into the K.I.D. do vary, as there are many ways in which the K.I.D. hardware, firmware, and software can be conjoined and the output monitored. There are platforms and technologies that have been designed that enable new devices and multimedia software to be leveraged broadly, which include but are not limited to:

The Internet;

Broadband wireless protocols (e.g. 802.11g, BLUETOOTH, PAN's and WPAN's technologies);

Computers (e.g. MICROSOFT WINDOWS OS, APPLE MACINTOSH OS, LINUX operating systems);

Proprietary Game Platforms (e.g. MICROSOFT X-BOX, NINTENDO GAME-CUBE, SONY PLAYSTATION2 systems);

Cable TV;

Game ready TVs and Home Entertainment Systems; and

Multimedia cellular devices and PDAs.

With this array of leveragable technologies some embodiments of the K.I.D. may be developed as a "Game Controller" with its software created in compliance with the specifications of that given platform, or it can have all the required technologies imbedded within its form and housing as a stand-alone device. The platform may be battery powered when low-power-consumption components are leveraged in its design, or it can plug into household current when this level of power is required or it can generate its own power via rechargeable batteries/capacitors charged through user operation.

DETAILED DESCRIPTION OF THE INVENTION

The preferred embodiments of the present invention relate to an a system and method for interactive, sustained, and immersive learning in a virtual environment having a user-controllable self-reference frame while in an active state. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

The ActiveLearning method and K.I.D. invention is designed for and intended to leverage a plurality of installed technologies and systems as well as low-cost components that allow systems to be cost-effective and self-contained when appropriate. One important feature of the invention is the active interplay between the K.I.D. and the multimedia system/software it contains or is designed to work with, with the sustainable effect of an increase in the user's metabolic and physiological rates, and a corresponding increase in absorption and retention of information while he/she is active and learning.

Figure 2:
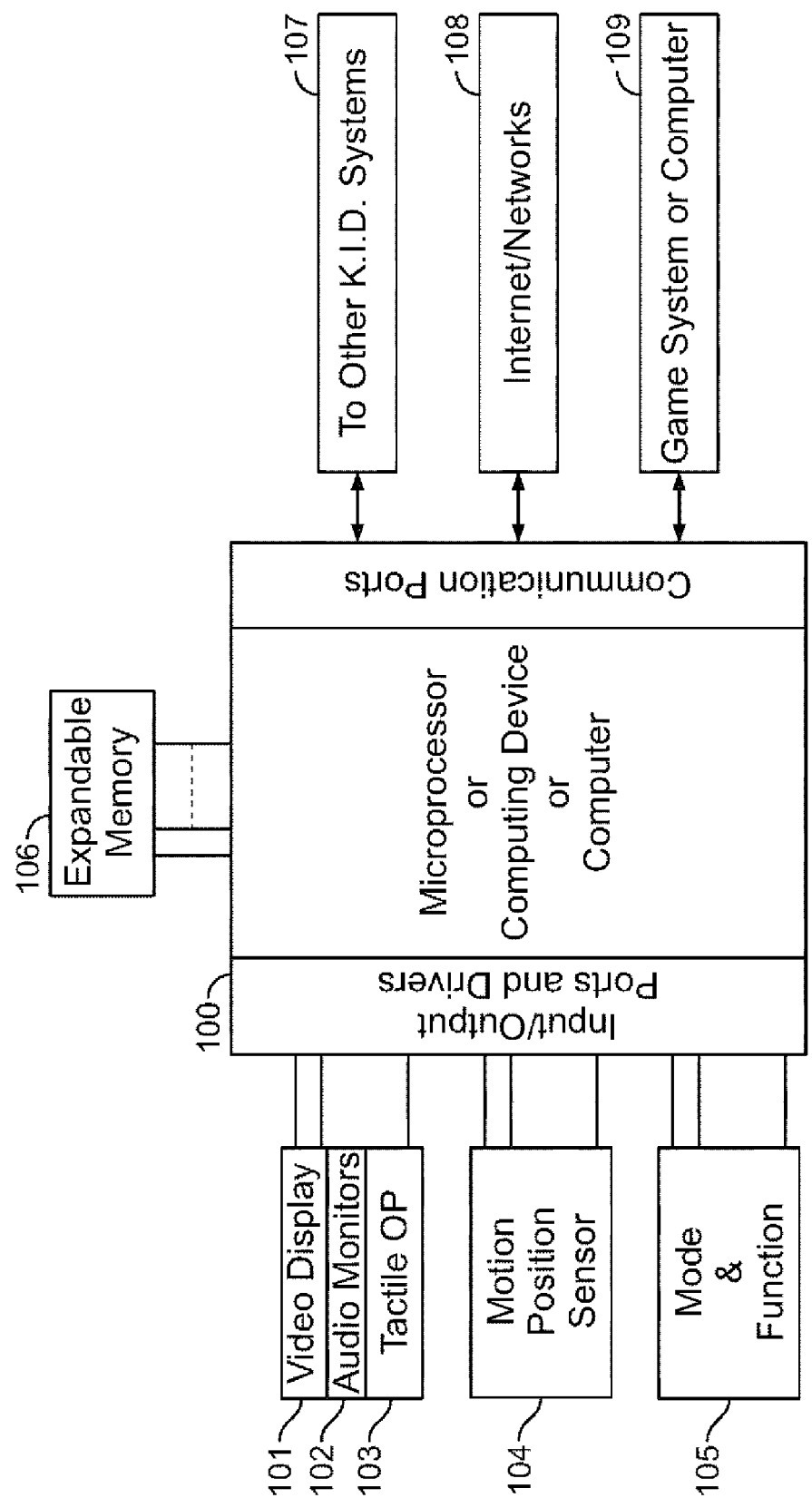
FIG. 2 is a functional block diagram of a preferred embodiment of the present invention.

FIG. 2 is a functional block diagram of a preferred embodiment of the present invention. The following descriptions refer to the components in FIG. 2:

100—Microprocessor or Computing device or Computer: includes one or more processors the K.I.D. may be designed to leverage, based upon specific implementation and feature requirements. Advantages of leveraging installed systems such as computers include recognition that their data, graphics and audio processing power is far superior to the stand alone processors used with low-cost multimedia toys and games. The microprocessor in a stand alone K.I.D. or in a computer the K.I.D. plugs into (e.g. via USB2) is responsible (in conjunction with software instructions) for providing signals appropriate for imaging system (101), audio monitoring (102) and output to drive tactile feedback (e.g., forced feedback in joysticks or vibration in seats and or handles) (103). Further microprocessor 100 provides feedback via binary code to the user based on user inputs such as motion (104) or force as may be measured by a plurality of sensors including buttons, pedals, levers, touch-screens and the like. Input options may include selection of a mode or function (105) in response to a lighted button, flashing menu screen, or an audio prompt requesting the user to make a selection. The response may be input by any number of switches or sensors triggered as before. Microprocessor 100 executes instructions sets it retrieves from a) its own internal registers and memory, b) external memory (106) or from other buses or communication ports that may be connected to other K.I.D.s (107), networks, and the Internet or other WAN (public or private) (108), or other game systems and their attendant memory and networks (109).

Microprocessor 100 or embedded MCU (Main Control Unit) is a single chip multiprocessor such as SSD's Super Xavix or a multimedia chip-set such as an SPG-240 chip manufactured by Sunplus Technology Co., Ltd., including a central processing unit (CPU), a picture processing unit (PPU) and a sound processing unit (SPU) able to create the graphics and sound corresponding to the simulated environment for display on the video display system. Similar chips are available from a host of companies such as Winbond, Holtek, King Billion, and the like.

101—Imaging System (e.g., video display): refers to a plurality of technologies (e.g. LCD, Plasma, CRT, DLP) that produce a static or moving picture from an electronic signal. These technologies may be external to the K.I.D. such as a TV, Home Theater, or Computer Monitor depending on the configuration and technology in the K.I.D. Likewise these technologies may be built onto or within the K.I.D. as an integrated component required or desired for sensory feedback or other interaction instruction or cue to the user.

102—Audio Monitor (or Speaker): includes a variety of technologies (e.g. Dynamic, Piezo, or Electrostatic) devised to amplify audio signals as a means of sensory feedback or other interaction instruction or cue to the user. Additionally monitors may be but are not limited to ear-buds, headsets, or bone induction devices. Audio Monitors may be external to the K.I.D. but could easily be built into the device or accessed via a headset and audio jack. Ear-buds and headsets have the advantage of delivering good quality audio while keeping the learning environment quiet.

103—Tactile Output: includes vibration (e.g. vibratory motors, low-frequency speakers), force feedback flight controller, wind, mist and the like, produced by a number of mechanisms or electrical devices that can be actuated by the microprocessor (100) or MCU as another means of sensory feedback, interaction instruction, or cue.

104—Motion Position Sensor: includes a host of switches, triggers, sensors, and methods for sensing or measuring speed, direction, orientation, force, height, weight, temperature, and the like as appropriate for the specific implementation. A rheostat, magnetic switch, or potentiometer, for example, could be used to measure a handlebar turning. Similarly there are a plurality of sensors (e.g. optical encoder like those found in certain mechanical computer mice) that may be used to determine a speed and direction of an axle, for instance. Piezo crystals may include accelerometers or strain-gauges for determining force or acceleration. All these (but not limited to these) sensor types may be used in a K.I.D. to provide input to microprocessor 100 and software logic will use at least a portion of this input as feedback to the interactive software program.

105—Mode and Function: includes types of feedback usually selected via buttons or other simple interface system. In the case of certain K.I.D.s the input could be "execute a left turn to quit" as the turning sensor and handlebars may be used in a modal sense to, for example, create the illusion of steering or to select items from an on-screen menu.

106—Expandable Memory: includes many types of volatile or non-volatile, removable or non-removable memory able to interface with microprocessor (100) MCU and the Operating System, such as read only memory (ROM), flash memory, compact disk, digital video disk, magnetic tape and the like. The instructions and data stored on expandable memory help the MCU, Operating System to perform the following functions: create a simulated environment, instructions, voice, sound effects, music and tactile feedback, as well as all on-screen images, animations and digital video designed to encourage interaction with the K.I.D., the simulated on-screen environment, and interface.

107—Other K.I.D. systems: includes a number of protocols and their associated transports designed to allow two or more K.I.D.s to interact, share data, or play simultaneously on a single AV system such as a Home Theater, game ready and/or cable TV, or computer monitor or display/imaging system. There are a number of physical specifications and communications protocol standards for the short range exchange of data over personal area networks (PANs) and wireless PANs. IrDA, Bluetooth and 802.11 are a few that could be leveraged within a K.I.D.

108—Internet/Networks: includes the worldwide web and the myriad of wired and wireless access points available to K.I.D. for access to computational power or content, public, private, and/or mixed. K.I.D. with internet access and robust processing speed (locally or over the Internet) could have access to endless rich media and ActiveLearning experiences through specially designed content and curricula accessible through new ActiveLearning sites. K.I.D.'s may have sensors and Internet protocol chips internally and run otherwise over the Internet.

109—Game System or Computer: includes a K.I.D. designed to use an external and more powerful microprocessor in lieu of, or in addition to, an embedded MCU found in a computer or gaming system. Current PCs and gaming computers have extremely robust architectures for creating and managing rich media (such as real-time 3-D environments, 5.1 Audio, and multi-user support).

Possible iterations and alternate embodiments of the ActiveLearning Method and K.I.D.s: Alternative ActiveLearning Method and K.I.D.s may be designed and built to leverage a plurality of mature technologies and platforms as well as others that are currently emerging. The preferred embodiment of any one K.I.D. will have several iterations and evolve as technologies become more robust, multimedia/network capable and cost effective. The concept and invention of ActiveLearning requires that the K.I.D. leverage the latest and greatest computational firmware and software in order that the quality of the interactive multimedia experience be as compelling as possible.

Figure 3:
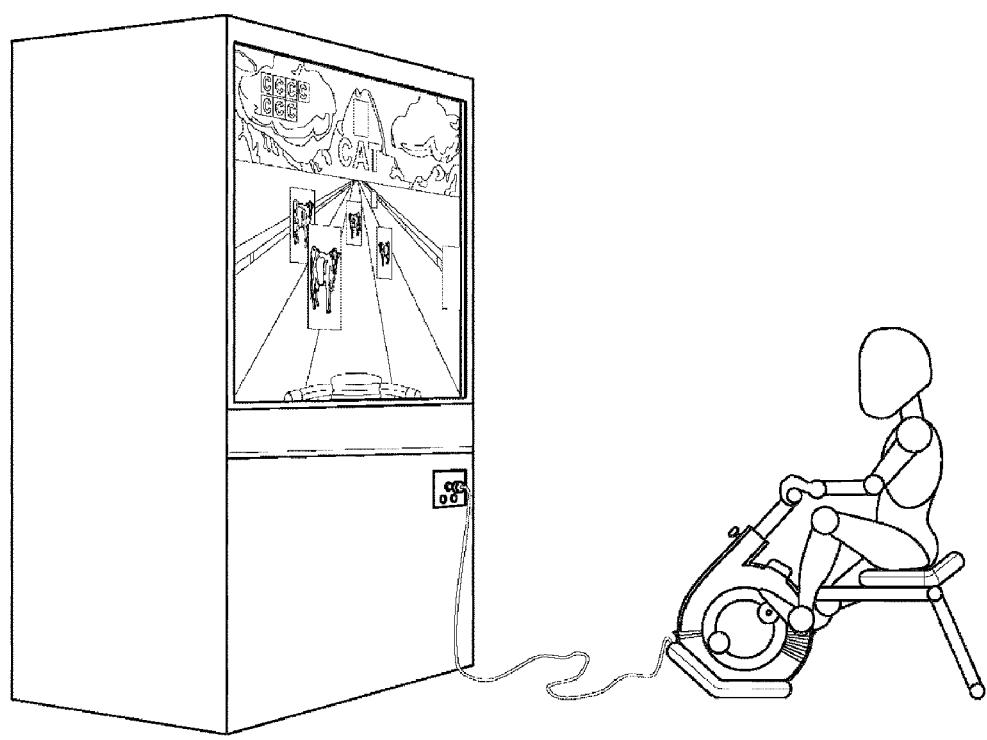
FIG. 3 is a perspective view of an embodiment of the present invention having a turn-2-learn smart kinetic interactive device connected via an RCA cable to a home entertainment system.

FIG. 3 is a perspective view of a system 300 having a turn-to-learn smart kinetic interactive device 305 connected via an RCA cable 310 to a home entertainment system 315. System 300, preferably, is a Plug-and-Play version of a Turn-2-Learn (a) Educycle that is operatively coupled to a video display system such as a television or home theater for example via 3 wires (2 stereo audio and 1 video cable). As further explained below, a frame of reference 320 for the user (e.g., a virtual representation of handlebars of K.I.D. 305) is supported in a learning, immersive virtual environment 325. Frame of reference 320 and environment 325 is responsive to user operation of KID 305 (e.g., pedaling to locate reference 320 in environment 325 and simulated turning of reference 320 when the user steers). Further details of the configuration, operation, and interaction of the environment, the reference, and the K.I.D. are disclosed herein.

When the K.I.D. is coupled to the audio/video display system it provides the user with an opportunity to engage in physical activity while simultaneously engaging in interactive learning by "traveling" in a simulated environment (e.g. a pseudo-3D world created with 2-D graphics or real-time 3-D environment, supported by sounds and music) played through the large-screen TV's audio visual system.

Important to preferred embodiments of the K.I.D. (Kinetic-Interactive-Device) and certain other implementations of the present invention is an ergonomically designed apparatus or piece of equipment significant to the ActiveLearning Instruction Delivery Methodology because its design (Examples, FIG. 4 and FIG. 5) encourages that the user engage in large and small body movement in order to maximize the immersive learning or play experience generated by the multimedia software. The ergonomic design is based on latest anthropometric data and safety guidelines for children's products to insure safety and comfort while creating an enhanced, immersive learning environment and "make-believe" quality for the child. A distinction of preferred embodiments of the present invention in contrast to some prior art systems is that the visual element facilitates learning derived from the environment while many prior art systems provide an environment (e.g., scrolling background) to ease some monotony of the exercise.

Figure 4:
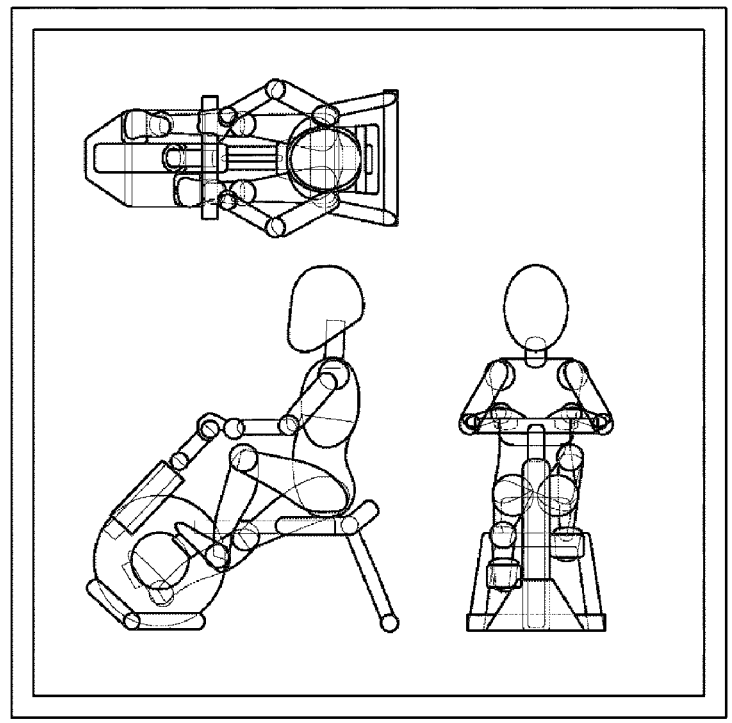
FIG. 4 is a set of views of an ergonomic design for a preferred embodiment of the present invention.

FIG. 4 is a set of views of an ergonomic design for a preferred embodiment of the present invention. In the preferred embodiments, a suitable ergonomic design is important to improved safety, function, and comfort. The ergonomic design enhances stationary sustained activity of large muscles (e.g., legs, arms, shoulders and the like).

Figure 5:
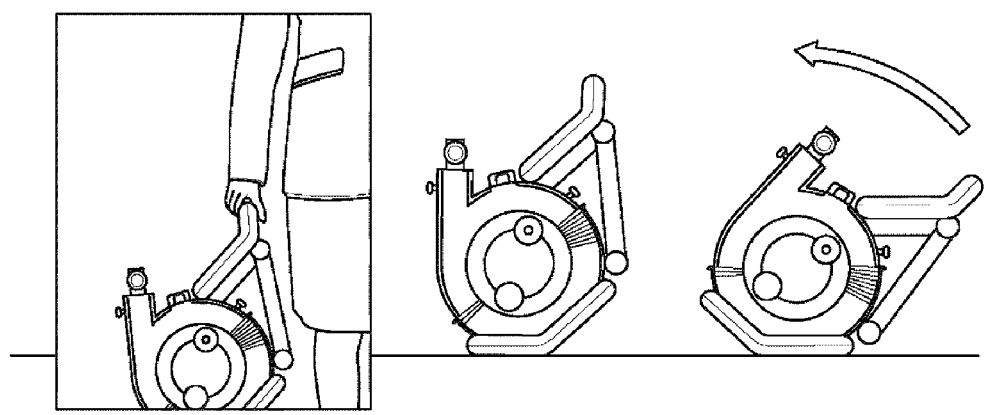
FIG. 5 is a view of a kinetic interactive device convertible between a deployed mode and a transportable mode.

FIG. 5 is a view of a kinetic interactive device convertible between a deployed mode and a transportable mode. In this embodiment, the ergonomic design parameters of FIG. 4 are also supplemented by providing for a compact device that is easy to carry and to store.

Qualities of the ergonomically designed K.I.D. are supported by associative software that extends opportunities of the form factor. The software for this Turn-2-Learn(a) "Plug-and-Play" Educycle is designed to take advantage of a stand alone MCU and pedal and turn interface. This first person/one point perspective view of this software coupled by the guard rails keeps the user "on road," but also keeps the perspective limited and the management of sprites and visual assets in line with the MCU's capabilities. These graphics in this embodiment are all 2-d and require knowledge of the chip's capabilities to derive a rich experience and reasonable depth of content and media.

Figure 6:
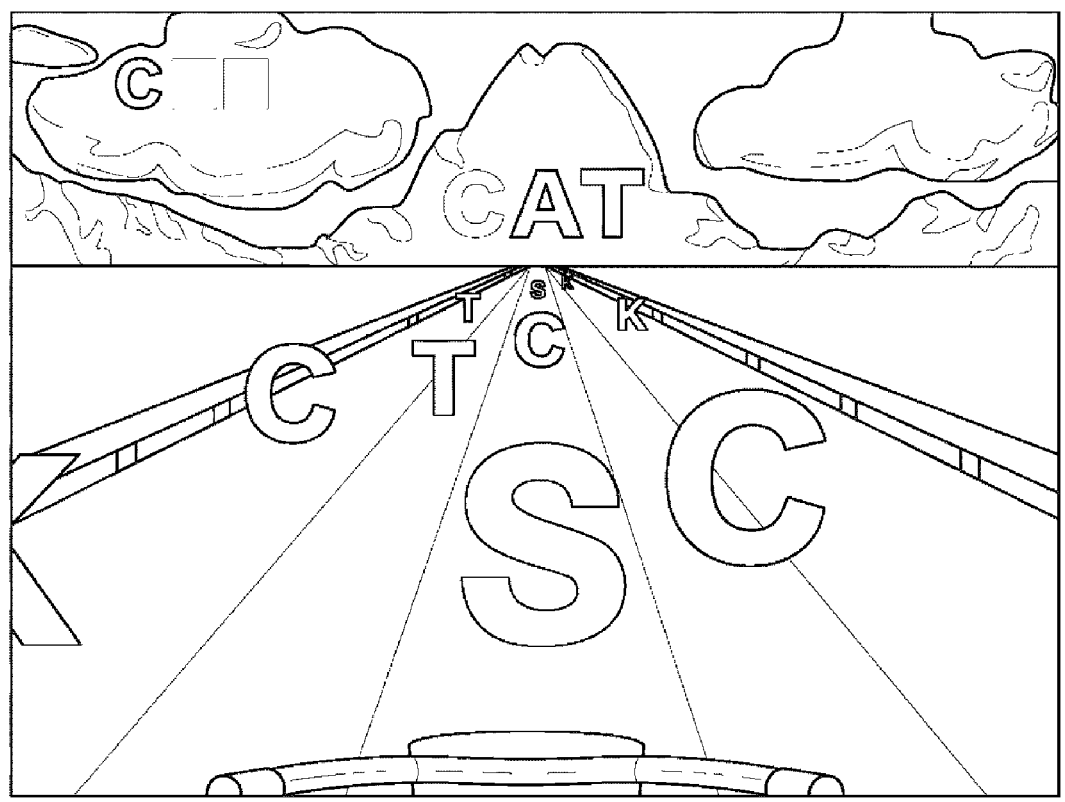
FIG. 6 is a first person perspective view of a first representative interface for a preferred embodiment of the present invention.

FIG. 6 is a first person perspective view of a first representative interface for a preferred embodiment of the present invention. FIG. 6 is a representation of one type of interface providing a first person perspective interface a user (e.g., a child) as the user pedals and turns to "collect" the requisite number of letter "C"s.

Figure 7:
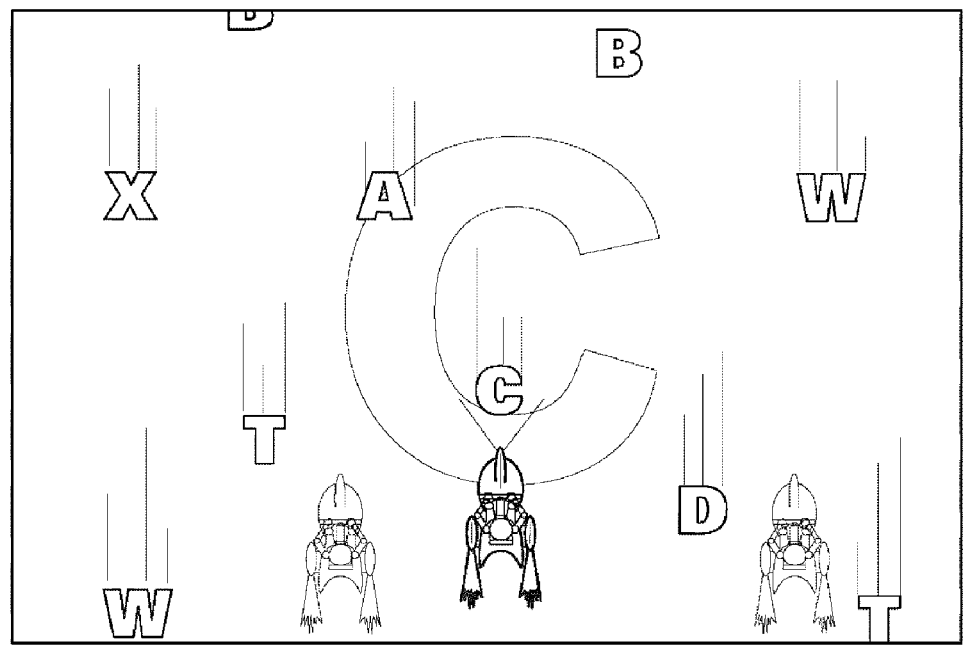
FIG. 7 is a first person perspective view of a second representative interface for a preferred embodiment of the present invention.

FIG. 7 is a first person perspective view of a second representative interface for a preferred embodiment of the present invention. FIG. 7 is a representation of another type of interface that provides ghosted images of a "rocket-trike" (lateral trike images to the central image) illustrating how turning moves the on-screen vehicle laterally left and right.

FIG. 6 and FIG. 7 illustrate two of many possible interface possibilities. FIG. 6 shows a road in one point perspective. Users can pedal and turn to navigate "down" the road with the objective of catching a specific letter in their basket (mounted on the on-screen handle-bars). In this instance the letter C is the target letter and appears on the mountain in the distance. The objective is to collect a given number of Cs to complete the word CAT. The faster the user pedals, the faster the letters will appear to come towards the user. The user must steer directly into the letter C to collect it and steer to avoid non-target letters. All the on-screen visual cues, sound effects, and music as well as the responsiveness of the sounds and visuals are a result of the software responding to sensors in the K.I.D. and user input.

In FIG. 7 there is a third person perspective (in top view) on the screen interface generated by the software (stored on cartridge memory) MCU and its Operating System. Again this interface and the animated sprites and multimedia assets preferably achieve good performance and still has a reasonable depth of content. This interface behaves differently, but for a user the illusion and subsequent immersion in learning while driving the ActiveLearning K.I.D. will be effective because the cause and effect of pedaling will be to make the on-screen "rocket-trike" move faster (as letters shower down faster) and it will move laterally left and right as the user steers to catch the letter C's in its "collector beam." The sound effects and moving graphics are again a result of the user's input, and the K.I.D.'s sensors interacting with the MCU and software. Integrated technologies—The K.I.D. may have the electronic display and the speaker(s) built into and integrated within the K.I.D.

Figure 8:
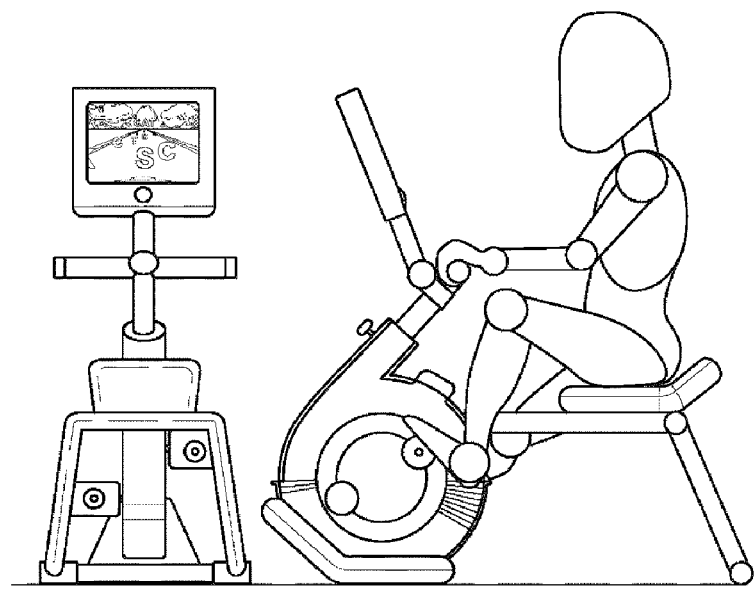
FIG. 8 is an alternate preferred embodiment of the present invention.

FIG. 8 is an alternate preferred embodiment of the present invention. FIG. 8 [Turn-2-Learn (b)] shows one configuration where the electronic display (e.g. LCD, Plasma, CRT or other) and speaker, along with the MCU, Operating System and associated Electronics, are mounted above the handle bars. Wires to the sensors in the pedals and handle bars mechanism, as well as wires to the software cartridge, run within the K.I.D.

Figure 9:
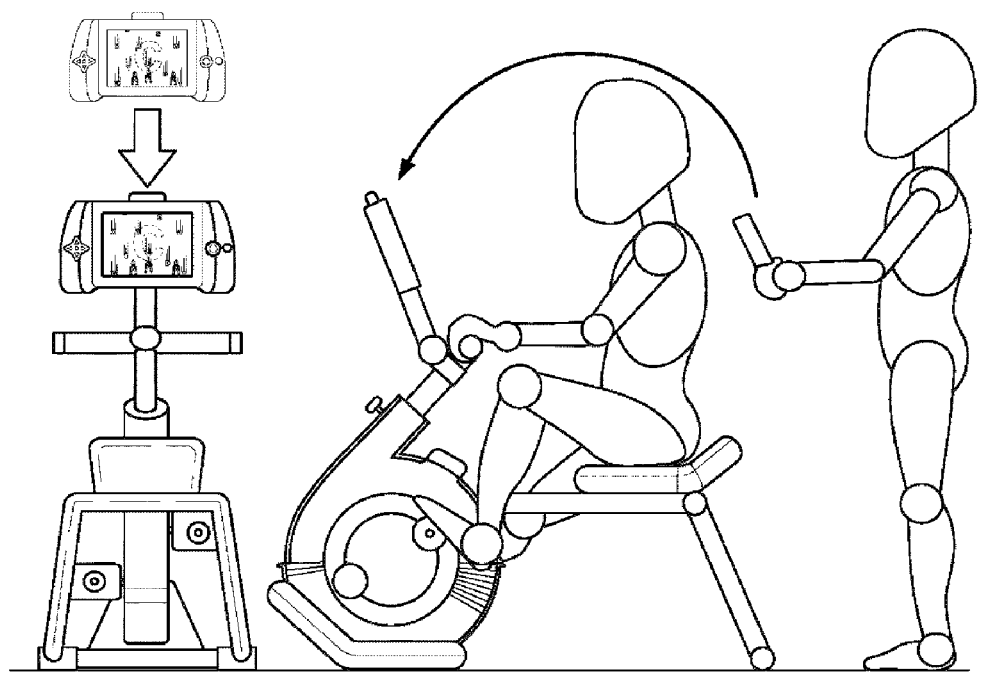
FIG. 9 is another alternate preferred embodiment of the present invention.

FIG. 9 is another alternate preferred embodiment of the present invention. FIG. 9 below [Turn-2-Learn (c)] combines a single integrated gaming unit similar to a Gameboy or Pixter with the K.I.D., where the handheld is securely attached to the K.I.D and the unit receives input (via electrical or wireless connections) from the K.I.D and its software (in cartridge) provides appropriate and coordinated feedback, visuals, and audio to the user's input via K.I.D. as it did as described above (for example, in FIG. 6) as a hard-wired, integrated system. The system shown in FIG. 9 has two modes: the visual imaging system provides an independent gaming system for a user disengaged from the activity device while permitting the user to engage the gaming system with the activity device to function as the K.I.D. system as described herein.

Figure 10:
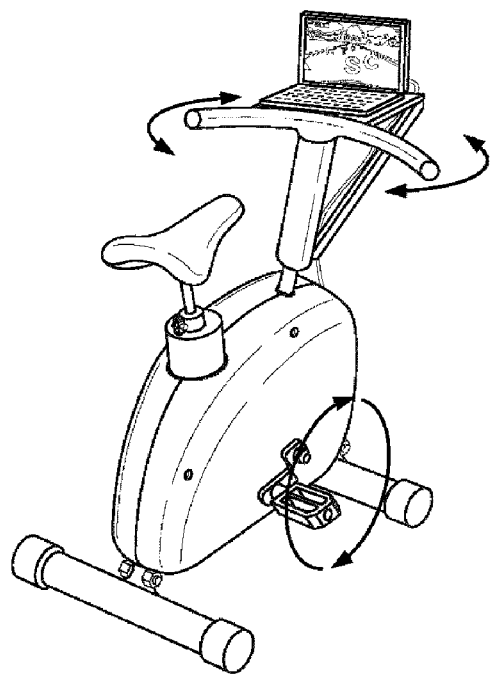
FIG. 10 is a Turn-2-Learn (d) Multimedia-laptop mounts via secure brackets onto specially designed K.I.D. and connects to an integrated ActiveLearning System.

FIG. 10 is system including a Turn-2-Learn (d) Multimedia-laptop that mounts via secure brackets onto specially designed K.I.D. and connects, for example via USB, for an integrated ActiveLearning System.

Figure 11:
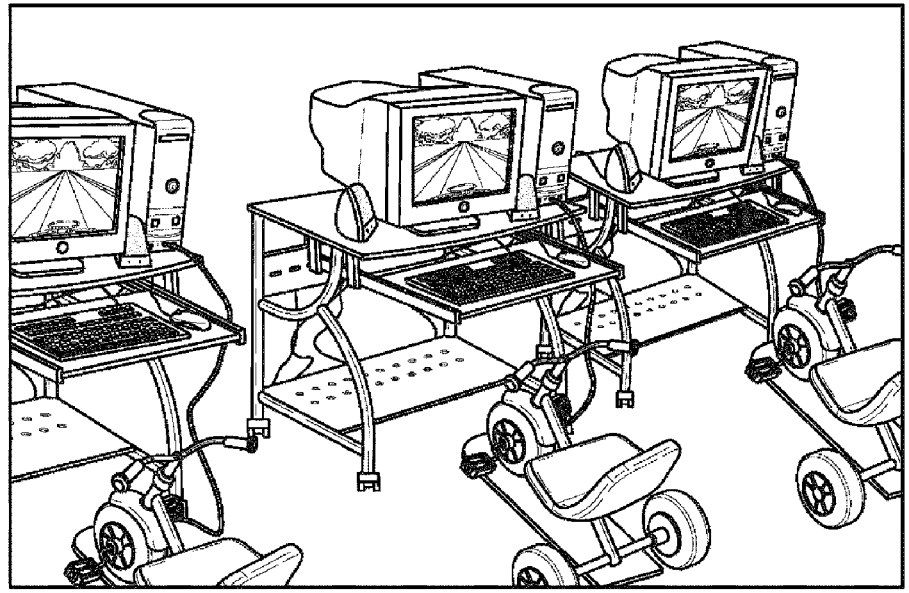
FIG. 11 is a Turn-2-Learn (e) K.I.D.s' adaptor connects a standard tricycle to a base unit-adaptor that leverages a powerful multimedia PC.

FIG. 11 is a system including a Turn-2-Learn (e) K.I.D.s' adaptor that couples a standard tricycle to a base unit-adaptor that leverages a powerful multimedia PC via a standard USB cable. The adaptor enables the user to use their "everyday" tricycle in a stationary mode that monitors pedaling and/or steering and provides interactivity signals to the software. The Turn-2-Learn(e) Educycle systems in FIG. 11 connect directly to powerful Desktop PCs with color monitors, graphics and stereo sound processors (all appropriate for their application and audience). Additionally these systems may be linked one to another via the computer's network capabilities and the ActiveLearning software design. This approach may also reduce a price of the K.I.D. because the K.I.D. leverages the investment already made in the user's PC. This configuration allows multiple players to compete, collaborate and learn together. These systems may also leverage conventional computer networks and the Internet. This opens opportunities for creating content distribution over the internet. It is possible to connect these systems wirelessly via WPAN (108).

Figure 12:
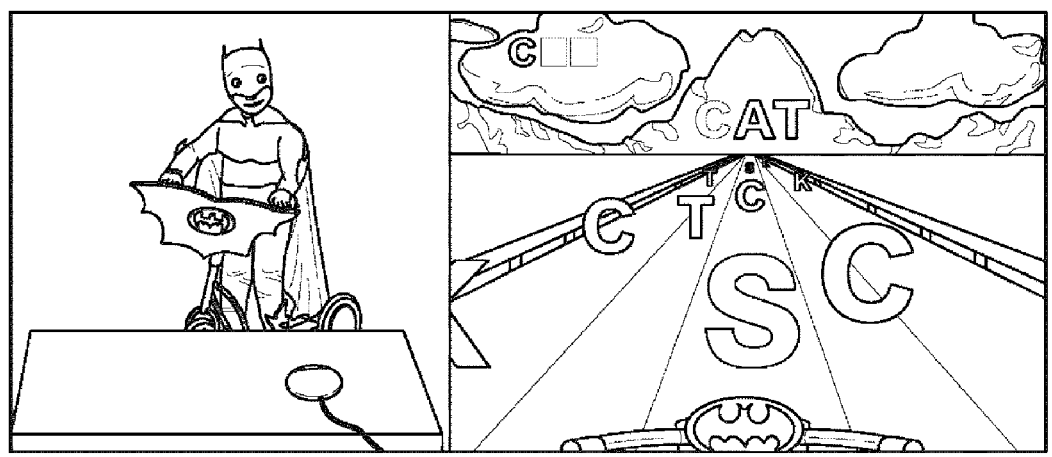
FIG. 12 illustrates an example of a smart (e.g., RFID tag/indicator) coordinated costume with K.I.D. accessories and onscreen tie-ins.

Accessories and Costumes—The K.I.D. may be accessorized to add functionality and new features. Specially designed K.I.D.s may have low cost sensors (e.g., RFID sensor(s)) built in that "recognize" any accessories which are attached to the K.I.D. Licensed products, themes, and role-play fantasies can be leveraged into the software, further enhancing the physical activity and immersive play experience that increases focus, reception, and retention of information. FIG. 12 illustrates an example of a coordinated costume with K.I.D. accessories and onscreen tie-ins. For example, some young children enjoy pretending to be "Batman" and the system may provide automatic detection when the user is in an appropriately designed costume to provide cues for the software/sensors to recognize, and/or provides the K.I.D. with suitable customizations ("bat fins on the tricycle or a bat symbol on the handlebars for example). As shown in the second panel of FIG. 12, the user frame of reference is customized to modify the reference. (However in some implementations, the environment and/or the curriculum may also, or instead of, be modified in this manner.)

Additionally, augmenting technology such as reflective IR inks, low cost RFID's, or magnetic switches can be incorporated into elements of the user's K.I.D. costume and/or accessories. For example, handlebar wraps, scooter faring, flags, bike helmet, knight's armor, superhero gloves, and the like, can initiate new on-screen sprites, audio and special powers. Additionally, on-screen tie-ins encourage the user to interact with the accessorized K.I.D and software to navigate new on-screen features and tasks and create sustained interest in the curriculum.

FIG. 3 shows the Turn-2-Learn (a) K.I.D. plugged into a large screen television with attendant audio speakers. The Turn-2-Learn K.I.D. is connected by means of three separate but commonly bound wire cables which have a video (yellow tipped) and audio (white and red tipped) RCA connector(s) which plug into the home entertainment's corresponding RCA video and stereo audio female connection jacks. These female jacks are found on the front and/or the back of many TVs and home entertainment systems or "game-ready" TVs.

Figure 13:
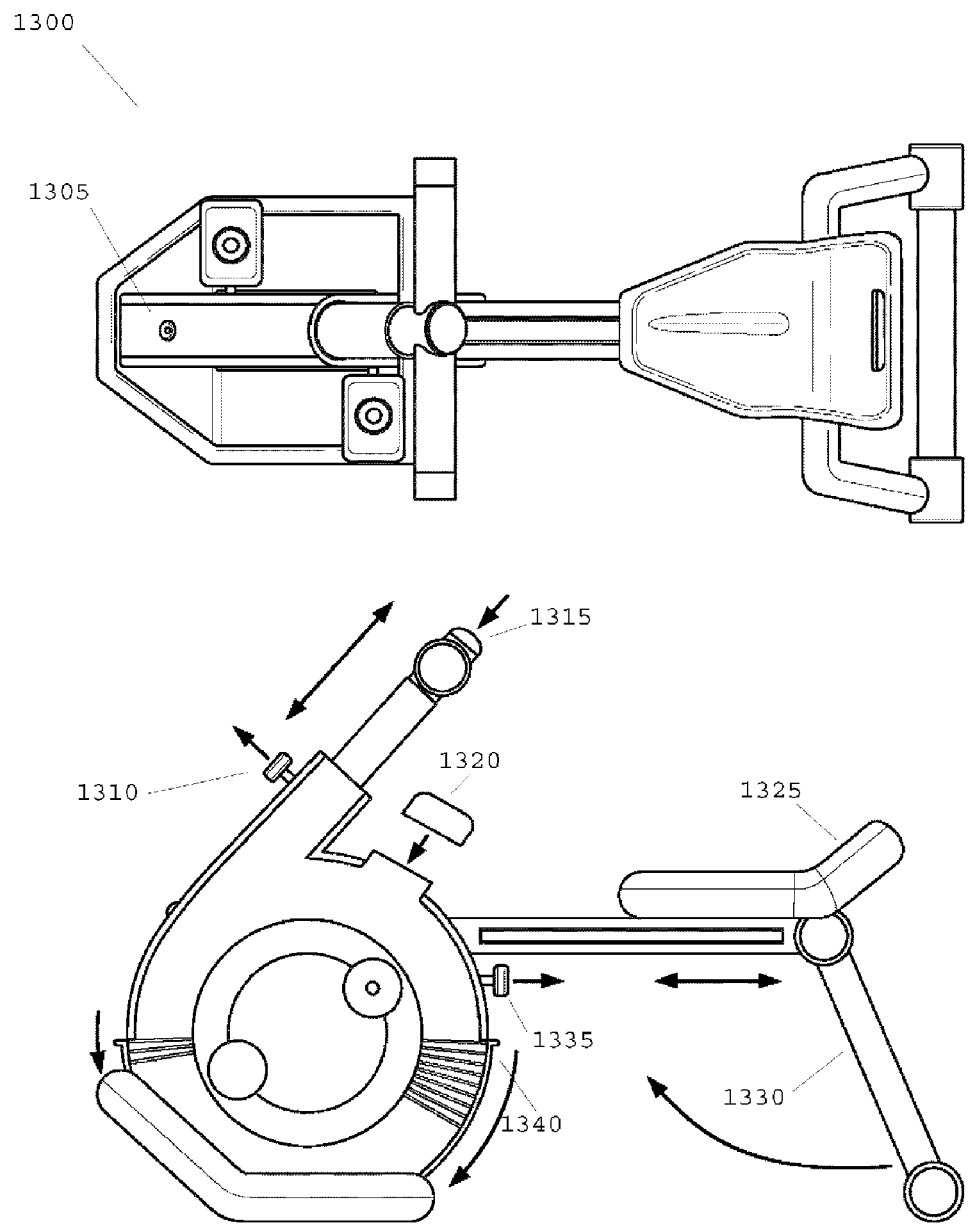
FIG. 13 is a detailed view of a kinetic interactive device detailing adjustability, compactability, and cartridge data expansion.

FIG. 13 is a detailed view of a representative kinetic interactive device 1300 described herein. Device 1300 includes one or more network devices 1305, a first pull-knob 1310 (used to extend/retract or otherwise adjust the handlebars), a horn 1315, a cartridge 1320 for mating to an expansion/curriculum slot, a combo seat back/handle 1325, a swing back leg 1330, a second pull-knob 1335 for controlling a seat sliding in and out, and a door 1340 for a storage area that could hold cartridges or other accessories.

Figure 1:
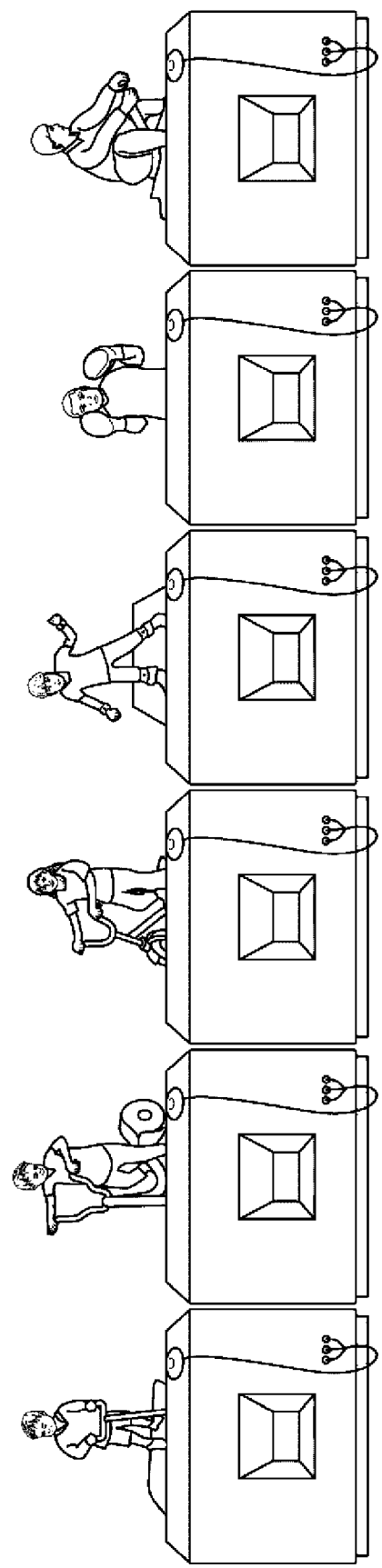
FIG. 1 is a perspective view of a set of representative preferred embodiments of the present invention.

Alternatively, the coupling may be any well known wireless data link, such as a radio frequency (RF) link or an infra-red (IR) link as depicted in FIG. 1. Here (FIG. 1, 12) the set-top unit communicates to the K.I.D. wirelessly and is connected to the TV via a wired connection.

Figure 14:
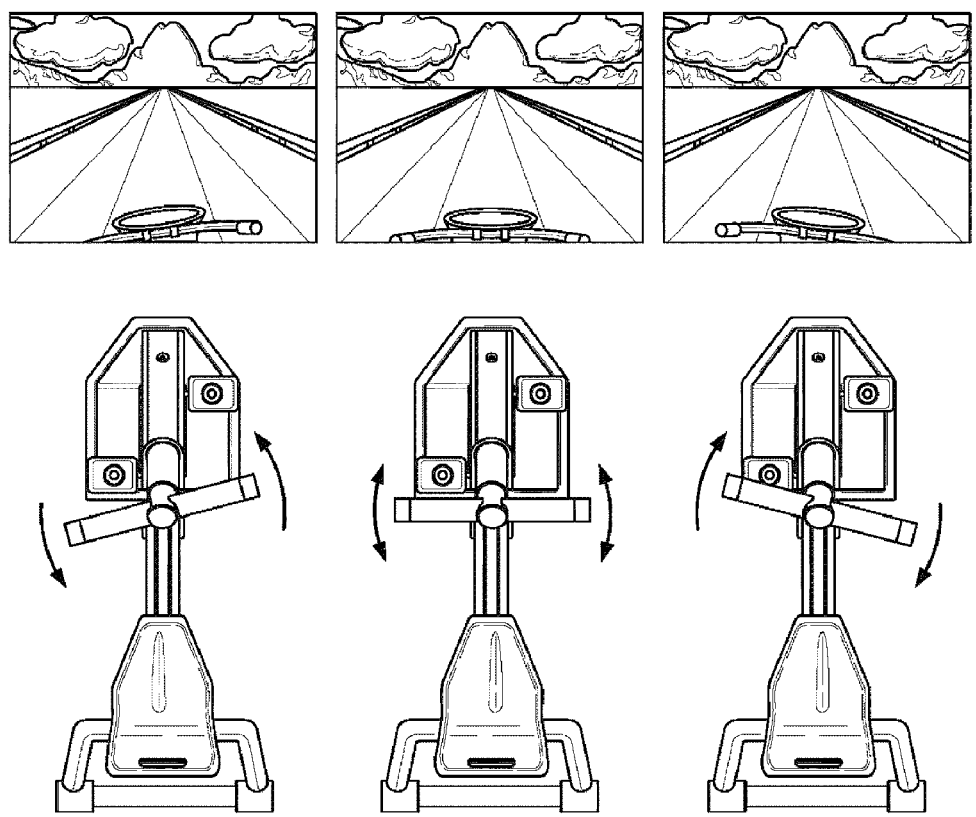
FIG. 14 is an illustration of immersion of a user reference frame of a kinetic interactive device into the supported environment.

FIG. 14 is an illustration of an example of immersion of a user reference frame of a kinetic interactive device into the supported environment. For example (as illustrated) a real left turn simulates a screen left turn of the environment while straight ahead handlebars cause the environment to appear straight ahead on-screen and a real right turn causes the environment screen to appear to make a right turn. These maneuvers may be incorporated into the apparatus to interact with learning content to accentuate the learning experience.

Turn-2-Learn (a) Educycle has built in sensors at the fulcrum of the handle bars to determine which direction the user is steering or turning. FIG. 14 illustrates how the onscreen software reacts to the position of the physical handle bars. Likewise, speed and direction (forward and back) sensors at the axle of the pedals detect pedaling speed and forward or backwards direction. Based on the software application the behaviors of these actions can vary. When the Turn-2-Learn (a) Educycle or K.I.D. is coupled to the TV it provides a child-user with an opportunity to engage in physical exercise while simultaneously engaging (becoming immersed) in interactive learning by "traveling" in a simulated environment (a real time 3-D environment or pseudo-3D world created with 2-D graphics, supported by environmental sounds and music) produced on the game-ready TV.

Figure 15:
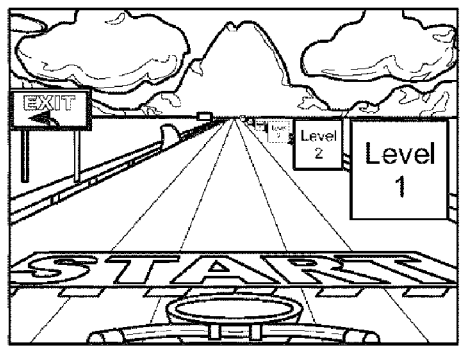
FIG. 15 is a detailed view of an interface for the present invention.

The interface and quality of graphics depends on the type of K.I.D., and associated processor and its processing power and the quality of the imaging system (101) and Audio (102) quality. FIG. 15 is a detailed view of a representative interface for the present invention. As shown earlier, this interface was designed to take advantage of the current preferred embodiment and shows a road in one point perspective with guard rails. If the user steers too far left or right, sound effects of metal scraping and screeching of rubber sounds let the user know to stop steering into the side rail. Off ramps provide rest branches to other types of activities. The "level" signs provide a way for user to select a level without traditional menu selection. Just pedal down the road and drive into the level of choice. This is an example of how the interface design enables a user to interact using large muscles only as clicking, pushing buttons, and other operations of the small muscles of the hand and the like are not required.

As shown in FIG. 6 and FIG. 7 the user is able to navigate down the road and collect the letters that comprise a word, or collect a picture of the word displayed on the distant mountain, and the like. Fun motivational music and sound effects make the journey exciting!

Various activities include, but are not limited to, learning encounters, creative activities, and arcade-like games further disclosed below. Numerous alternate preferred embodiments of the kinetic-interactive-device K.I.D are within the scope of the present invention. For example, in addition to the apparatus of the Turn-2-Learn Educycle the apparatus of other embodiments may be configured as seen in FIG. 1, Table I, Table II, or elsewhere herein:

TABLE I

| Trampoline & Handlebars (Jump-2-Learn) | Activity System w/Appendage Sensor(s) (Dance-2-Learn) |
|---|---|
| Stepper (Climb-2-Learn | Rowing (Row-2-Learn) |
| Scooter (Scoot-2-Learn) | Bounce (Bounce-2-Learn |
| Boxing (Box-2-Learn | Horse Riding (Gallop-2-Learn) |

ActiveLearning method and the plurality of kinetic interactive devices K.I.D.s enabling the user to engage in musculoskeletal exercise are by no means limited to these items or configurations. Further, the learning encounters and arcade-like games for any of the preferred embodiments may correspond to a wide range of curricula items, such as those described in Table 1 below.

Multimedia System/Software Curriculum:

As previously stated, an important aspect of the ActiveLearning methodology and invention embodiments includes an active interplay between the K.I.D. and the multimedia system/software it contains or is designed to work with, with the sustainable effect of an increase in the user's metabolic and physiological rates and a demonstrable corresponding increase in absorption and retention of information while he/she is learning.

ActiveLearning multimedia system/software curriculum specially designed to work in correspondence with the K.I.D.s will have the following features:

Multimedia-based system/software curriculum will mimic the fundamental immersive quality of play by combining physical activity, the delivery of information and concepts correlated to physical actions, and the power of imagination.

Interactive intellectual activities, themes, and narratives in the curriculum will be consistently tied to and correspond with children's physical movement and kinetic input on the K.I.D. User's physical activity while playing on a kinetic-interactive-device (K.I.D.) can and will include both sustained large muscle movement as well as large muscle movement and may further, in some embodiments, be punctuated by resting pauses and small muscle activities.

Succinctly put, representative ActiveLearning curriculum will be selectively designed, coherently integrating physical activity, imagination, and learning of new information and concepts. Curriculum will focus on explorations, navigations, themes, stories, and/or narratives contextualized with both K.I.D. input and the imagination of the user, mimicking the immersive quality of play.

Curriculum areas shall include but are not limited to:

TABLE II

| Languages (various): | Music |
|---|---|
| Letters | Notes (high, low, soft, loud, |
| Shapes (upper and lower case) | short, long) |
| Sounds | Instruments and Their Sounds |
| Names | Bands and orchestras |
| Spelling | Math |
| Vowels | Numbers |
| Consonants | Shapes |
| Vowel and Consonant Blends | Names |
| Vocabulary | Values |
| Words and Meanings | Counting |
| Synonyms | Addition & Subtraction |
| Antonyms | Simple Fractions |
| Life Science: | Piggy-Bank Math (Money) |
| Human Body | Visual Arts |
| Body Parts | Shapes |
| How Things Work | Colors |
| Hygiene and Growing | Sizes |
| Plants and Animals | Spatial Relationships |
| Flying Animals | Over/Under |
| Life Under Water | Inside/Outside |
| Food Chains | Behind/In-front |
| Diet and Exercise | Patterns |
| Space: | History |
| Planet Earth and the Sun | Long-Ago Creatures |
| Our Solar System | (Dinosaurs to Dodos) |
| Moon and Stars | Past People and Ways |
| Physics | America (Pilgrims to Present) |
| Gravity | |
| Distance | |
| Speed | |
| Measuring | |

Possible Curriculum Features:

Example: Driving Mode for Turn-2-Learn (a)

As the user begins to pedal on the K.I.D. [Turn-2-Learn (a)], she'll make her way "down the path" of learning vis-à-vis the software/multimedia system. The software interacts with and in that way "documents" the user's physical journey on the K.I.D. through the software's exploratory, multimedia-based world. For example, there may be a direct correlation between the speed at which the user pedals and the speed at which he/she moves through the landscape or story provided by the software/multimedia system. When the user stops pedaling, the bike on screen may "coast" to a stop rather than stopping immediately. Pedaling backward may bring the user more quickly to a stop, or the user may begin to move backwards through the "documentary," reviewing previous presentations of information or concepts. Faster pedaling may also allow a user to view more information more quickly.

Similarly, the turning of the K.I.D.'s handlebars may determine which "path" the story takes, or which piece of information is learned next.

Example: A user's Turn-2-Learn (a) could be accessorized to resemble a rocket ship. Specially designed software takes the user "into space," naming and providing information on the moon, space stations, and planets as they are passed by—based on the speed of the user's pedaling or on turns of the handlebar—and revealing "surprise rewards" based on correct answers entered into interactive buttons on the handlebars.

Example: Specially designed software may focus on a particular set of "collectables" as part of a learning objective. For instance, software associated with a user's Turn-2-Learn (a) may use the "road" as a metaphor for the journey of learning. One stretch of road may have the user identify and collect numbers 1-10, while another road segment may have the user collect all the vowels. As a desired item is collected (e.g., by driving over it or by other means), it may be placed in a score box. When the user is collecting vowels, and he/she drives over a consonant, a funny sound effect may be produced with no score credited. There may also be "road hazards" that the user might want to avoid, such as going off the road or stopping pedaling at an inopportune time.

Example: Specially designed software associated with a user's Turn-2-Learn (a) may allow for "off-ramps," enabling the user to exit off the "main road" by turning the handlebars. "Off-ramps" may take the child into new areas of academic or intellectual exploration based on their own curiosity. "Off-ramps" may also offer the user a chance to take a break from pedaling and engage in small muscle activity. Additionally, the interface may include level selectors that require the user to use the interactive device to position/maneuver the frame-of-reference to select an curriculum level.

Example: Specially designed software and networked K.I.D.s may allow for Single Player Mode, which enables the user to either race against the clock or race against chosen opponents in a head-to-head physical or mental challenge, or Multiple Player Mode, where each user will take a turn or simultaneously compete in a head-to-head physical or mental challenge against the same opponents.

Fun "rewards" deliverable via a host of methods. Again, with stand alone systems, assets and media are limited but there are cheap tricks that can be fun and very rewarding for users as discovered during market testing of this product.

Figure 16:
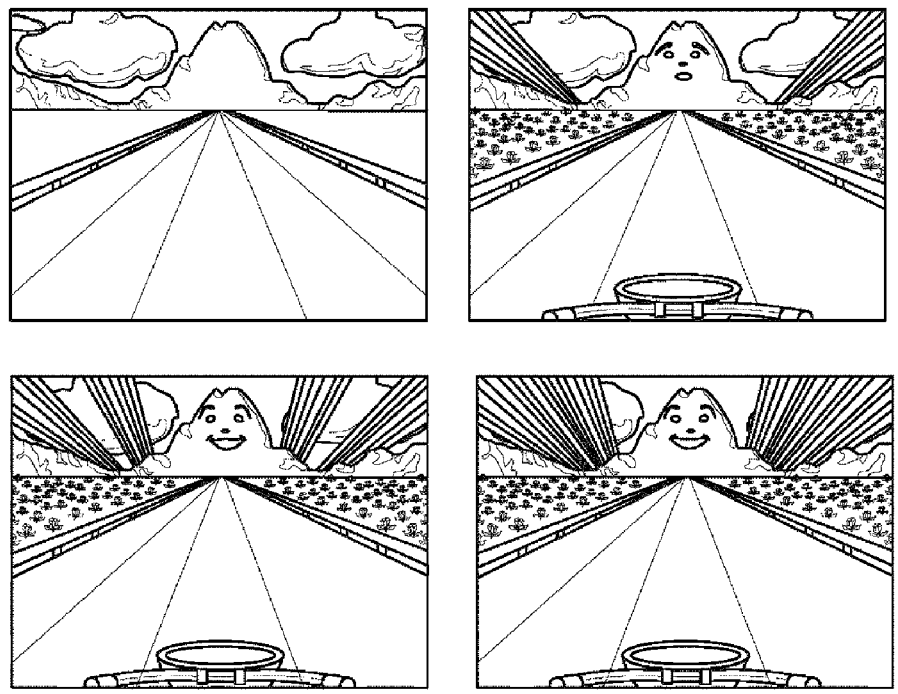
FIG. 16 is a detailed view of an interface of the present invention relating to a rewards system.

FIG. 16 is a detailed view of an interface of the present invention relating to a rewards system. Consider the four screens of FIG. 16: the character on the distant mountain display looks of surprise and congratulations. This character may, in some embodiments, be a helper or coach during learning exercises. In this scenario, a user upon completion of a task would be able to view one of these three screens with cheerful accompanying sound bytes.

Figure 17:
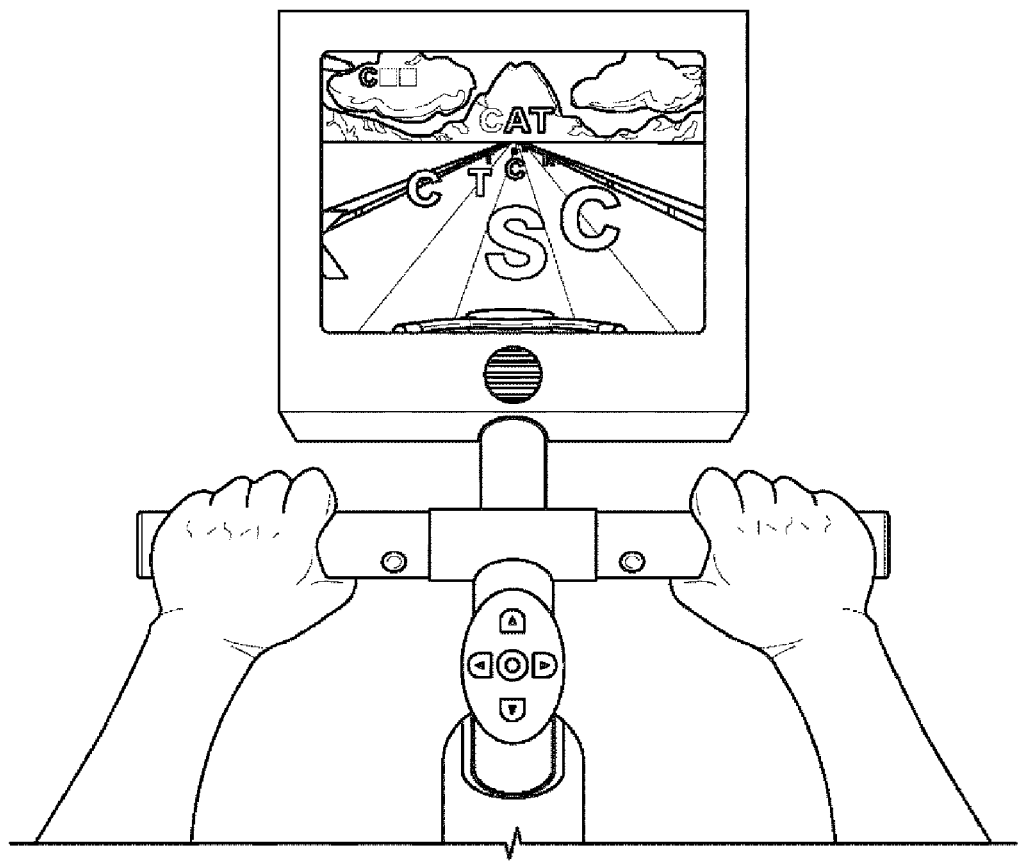
FIG. 17 is a detailed view of a turn/pedal/button interface.

FIG. 17 is a detailed view of a turn/pedal/button interface. As the user turns the real-world handlebars, the in-environment handlebars turn to direct the user to the desired letter and/or avoid the non-desired letters.

Figure 18:
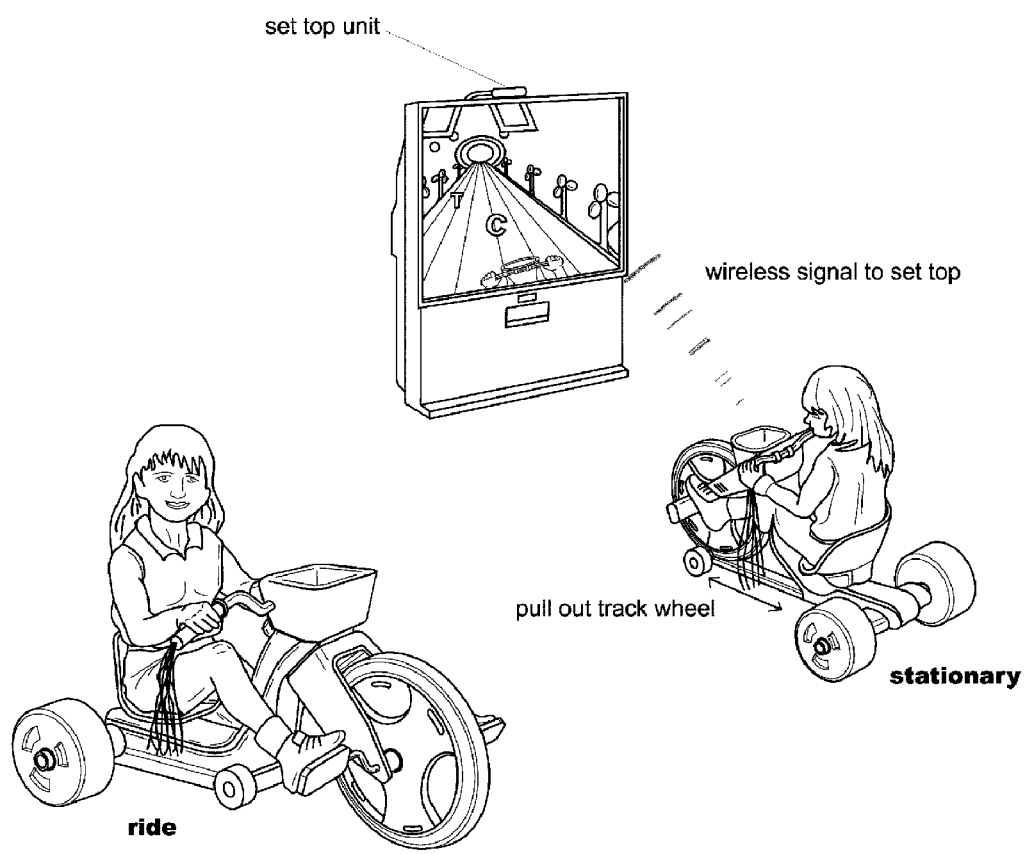
FIG. 18 is a detailed view of a convertible kinetic interactive device.

FIG. 18 is a detailed view of a convertible kinetic interactive device. In FIG. 1 a real working tricycle is useable in an ActiveLearning system. As shown, an adaptor is built-into the tricycle that pulls out (e.g., slides forward from a stowed mode to an engaged mode) to engage the drive wheel and permit stationary operation. The act of pulling out the adaptor turns the wireless communication system on. (In some embodiments, the user's pedaling charges a battery for the wireless system or there may be replaceable batteries.) A cartridge-based set-top receiver interfaces with the wireless signal as described herein.

Figure 19:
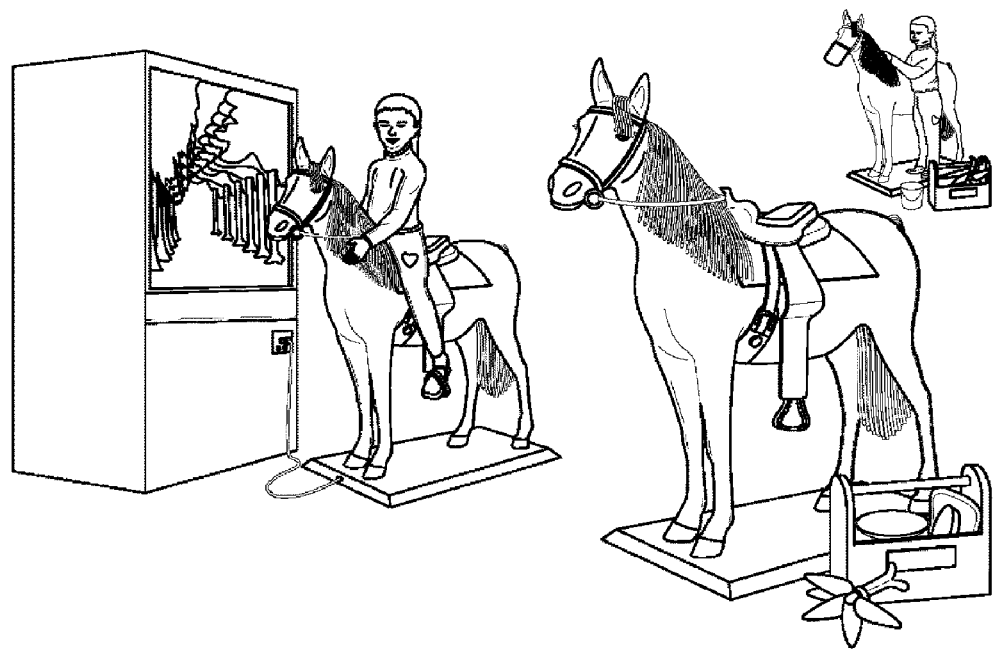
FIG. 19 is a perspective view of an alternate kinetic interactive device.

FIG. 19 is a perspective view of an alternate kinetic interactive device fashioned as a riding animal (e.g., a horse). The riding animal K.I.D. for interactive learning by simulating riding instruction or using the horse device as an interface to the instructional system also provides the interaction with the software and associated audio/visual tactile feedback. Here, other sensors may be used to encourage caring, nurturing, and/or grooming in addition to the riding activity.

Figure 20:
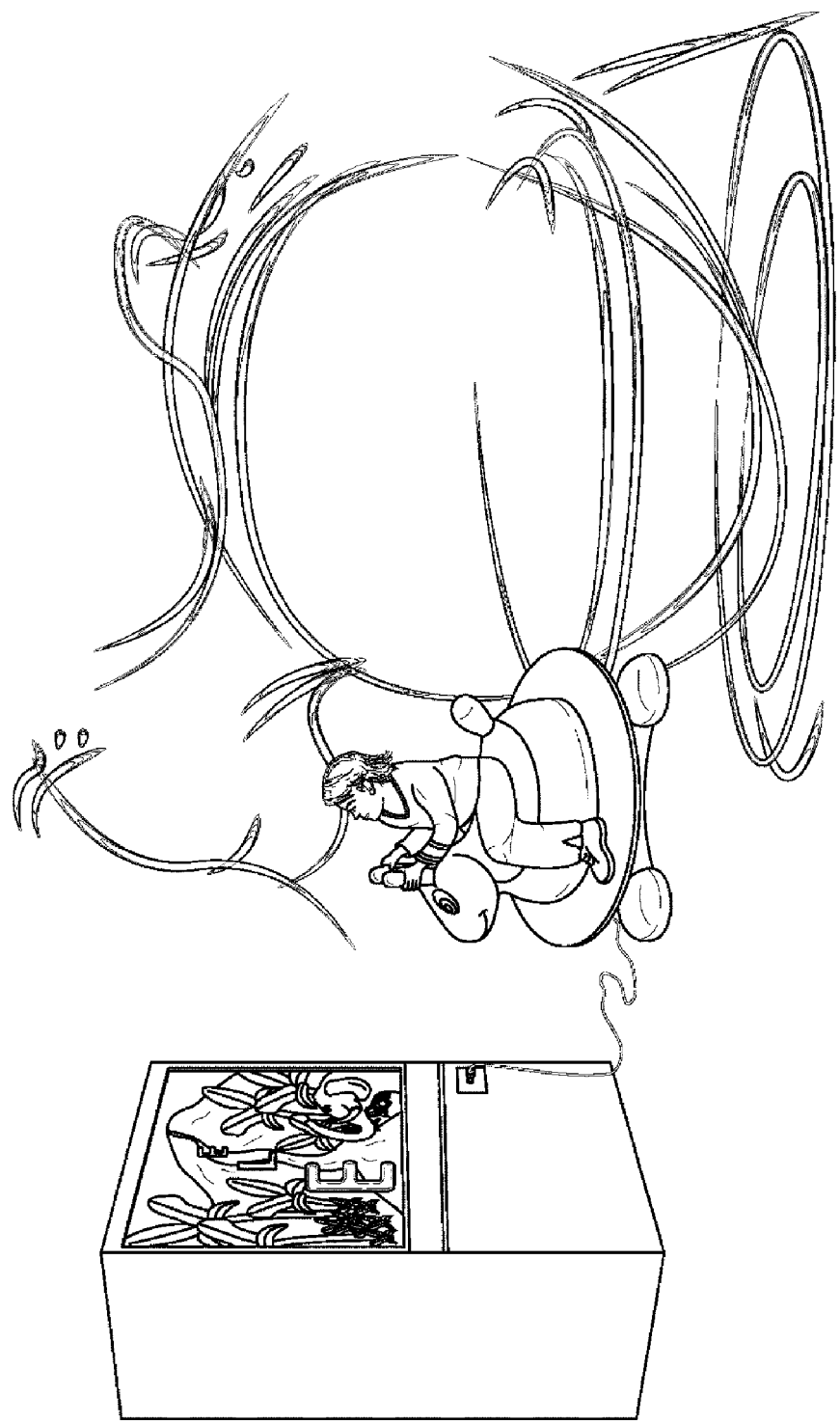
FIG. 20 is a perspective view of another alternate kinetic interactive device.

FIG. 20 is a perspective view of another alternate kinetic interactive device for a bounce-2-learn. This interface may be suitable for certain users (e.g., very young) to have fun interacting with appropriate learning content that is also adapted for the "bouncing" interface.

Figure 21:
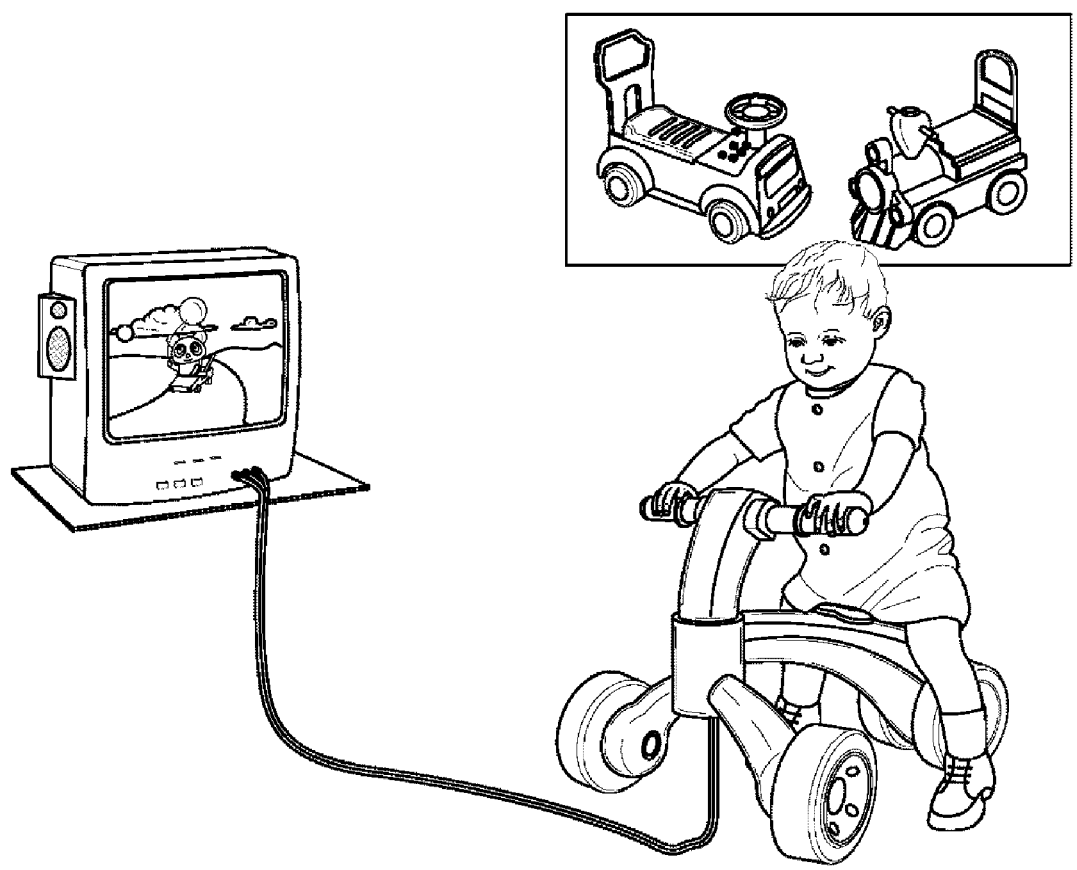
FIG. 21 is a perspective view of a third alternate kinetic interactive device.

FIG. 21 is a perspective view of a third alternate kinetic interactive device. The turn-2-learn is a simple embodiment for interacting with the software.

The system, method, computer program product, and propagated signal described in this application may, of course, be embodied in hardware; e.g., within or coupled to a Central Processing Unit ("CPU"), microprocessor, microcontroller, System on Chip "SOC"), or any other programmable device. Additionally, the system, method, computer program product, and propagated signal may be embodied in software (e.g., computer readable code, program code, instructions and/or data disposed in any form, such as source, object or machine language) disposed, for example, in a computer usable (e.g., readable) medium configured to store the software. Such software enables the function, fabrication, modeling, simulation, description and/or testing of the apparatus and processes described herein. For example, this can be accomplished through the use of general programming languages (e.g., C, C++), GDSII databases, hardware description languages (HDL) including Verilog HDL, VHDL, AHDL (Altera HDL) and so on, or other available programs, databases, nanoprocessing, and/or circuit (i.e., schematic) capture tools. Such software can be disposed in any known computer usable medium including semiconductor, magnetic disk, optical disc (e.g., CD-ROM, DVD-ROM, etc.) and as a computer data signal embodied in a computer usable (e.g., readable) transmission medium (e.g., carrier wave or any other medium including digital, optical, or analog-based medium). As such, the software can be transmitted over communication networks including the Internet and intranets, virtual private networks and/or local area networks. A system, method, computer program product, and propagated signal embodied in software may be included in a semiconductor intellectual property core (e.g., embodied in HDL) and transformed to hardware in the production of integrated circuits. Additionally, a system, method, computer program product, and propagated signal as described herein may be embodied as a combination of hardware and software, e.g., CPU, PROM, ROM, RAM and the like.

One of the preferred implementations of the present invention is as a routine in an operating system made up of programming steps or instructions resident in the memory of a computing system shown in the figures, during computer operations. Until required by the computer system, the program instructions may be stored in another readable medium, e.g. in a disk drive, or in a removable memory, such as a USB flash, an optical disk for use in a CD ROM computer input or in a floppy disk for use in a floppy disk drive computer input, disk drive or other portable or communicated memory system or the like. Further, the program instructions may be stored in the memory of another computer prior to use in the system of the present invention and transmitted over a LAN or a WAN, such as the Internet, when required by the user of the present invention. One skilled in the art should appreciate that the processes controlling the present invention are capable of being distributed in the form of computer readable media in a variety of forms.

Any suitable programming language can be used to implement the routines of the present invention including C, C++, Java, assembly language, etc. Different programming techniques can be employed such as procedural or object oriented. The routines can execute on a single processing device or multiple processors. Although the steps, operations or computations may be presented in a specific order, this order may be changed in different embodiments. In some embodiments, multiple steps shown as sequential in this specification can be performed at the same time. The sequence of operations described herein can be interrupted, suspended, or otherwise controlled by another process, such as an operating system, kernel, etc. The routines can operate in an operating system environment or as stand-alone routines occupying all, or a substantial part, of the system processing.

In the description herein, numerous specific details are provided, such as examples of components and/or methods, to provide a thorough understanding of embodiments of the present invention. One skilled in the relevant art will recognize, however, that an embodiment of the invention can be practiced without one or more of the specific details, or with other apparatus, systems, assemblies, methods, components, materials, parts, and/or the like. In other instances, well-known structures, materials, or operations are not specifically shown or described in detail to avoid obscuring aspects of embodiments of the present invention.

A "computer-readable medium" for purposes of embodiments of the present invention may be any medium that can contain, store, communicate, propagate, or transport the program, or expanded content including dynamic information including score, performance, grade, bookmark features, instructions (all or a portion thereof) for use by or in connection with the instruction execution system, apparatus, system or device. The computer readable medium can be, by way of example only but not by limitation, an electronic, magnetic, optical, electromagnetic, infrared, or semiconductor system, apparatus, system, device, propagation medium, or computer memory.

A "processor" or "process" includes any human, hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems.

Reference throughout this specification to "one embodiment", "an embodiment", or "a specific embodiment" means that a particular feature, structure, or characteristic described in connection with the embodiment is included in at least one embodiment of the present invention and not necessarily in all embodiments. Thus, respective appearances of the phrases "in one embodiment", "in an embodiment", or "in a specific embodiment" in various places throughout this specification are not necessarily referring to the same embodiment. Furthermore, the particular features, structures, or characteristics of any specific embodiment of the present invention may be combined in any suitable manner with one or more other embodiments. It is to be understood that other variations and modifications of the embodiments of the present invention described and illustrated herein are possible in light of the teachings herein and are to be considered as part of the spirit and scope of the present invention.

Embodiments of the invention may be implemented by using a programmed general purpose digital computer, by using application specific integrated circuits, programmable logic devices, field programmable gate arrays, optical, chemical, biological, quantum or nanoengineered systems, components and mechanisms may be used. In general, the functions of the present invention can be achieved by any means as is known in the art. Distributed, or networked systems, components and circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope of the present invention to implement a program or code that can be stored in a machine-readable medium to permit a computer to perform any of the methods described above.

Additionally, any signal arrows in the drawings/Figures should be considered only as exemplary, and not limiting, unless otherwise specifically noted. Furthermore, the term "or" as used herein is generally intended to mean "and/or" unless otherwise indicated. Combinations of components or steps will also be considered as being noted, where terminology is foreseen as rendering the ability to separate or combine is unclear.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

The foregoing description of illustrated embodiments of the present invention, including what is described in the Abstract, is not intended to be exhaustive or to limit the invention to the precise forms disclosed herein. While specific embodiments of, and examples for, the invention are described herein for illustrative purposes only, various equivalent modifications are possible within the spirit and scope of the present invention, as those skilled in the relevant art will recognize and appreciate. As indicated, these modifications may be made to the present invention in light of the foregoing description of illustrated embodiments of the present invention and are to be included within the spirit and scope of the present invention.

Thus, while the present invention has been described herein with reference to particular embodiments thereof, a latitude of modification, various changes and substitutions are intended in the foregoing disclosures, and it will be appreciated that in some instances some features of embodiments of the invention will be employed without a corresponding use of other features without departing from the scope and spirit of the invention as set forth. Therefore, many modifications may be made to adapt a particular situation or material to the essential scope and spirit of the present invention. It is intended that the invention not be limited to the particular terms used in following claims and/or to the particular embodiment disclosed as the best mode contemplated for carrying out this invention, but that the invention will include any and all embodiments and equivalents falling within the scope of the appended claims. Thus, the scope of the invention is to be determined solely by the appended claims.

What is claimed as new and desired to be protected by Letters Patent of the United States is:

1. An active learning apparatus, comprising:

an activity device including an activity sensor generating an activity interaction signal responsive to a sustained large-muscle physical activity of a user operating said activity device wherein said large-muscle physical activity results from sustained use of one or more large-muscles selected from the group consisting of arm large-muscle, leg large-muscle, shoulder large-muscle, and combinations thereof and wherein said activity interaction signal includes a motive element and a directional element;

a controller, coupled to said activity device, generating a virtual environment supporting a virtual user frame-of-reference in said virtual environment, said controller generating two or more virtual education elements in said environment and a goal for said virtual user frame of reference with respect to said virtual education elements, wherein said goal includes two or more independently-navigatable subgoals arranged in a goal sequence relative to one another, wherein said controller is responsive to said activity interaction signal to produce an affected interaction of said virtual user frame of reference with said virtual education elements with said controller measuring a conformation of said goal in said goal sequence by said affected interaction wherein said controller is responsive to said motive element to control a speed of said virtual user frame of reference in said virtual environment, wherein said controller is responsive to said directional element to control a direction of said virtual user frame of reference in said virtual environment, and wherein said virtual education elements are all independently-navigatable and concurrently presented in said virtual environment along with said goal including said subgoals with said user navigating said virtual user frame of reference through said virtual environment using said motive element and said directional element to interact with said virtual education elements responsive to said goal to select individual ones of said virtual elements in said goal sequence; and a feedback system, coupled to said controller, for presenting said virtual environment with said user frame-of-reference in relation to said virtual education elements for providing said user with feedback regarding said goal and said subgoals, and said conformation of said goal and subgoals in said goal sequence by said affected interaction;

wherein said education elements include both a first plurality of numerals and equation elements associated with said numerals wherein said first plurality of numerals and equation elements include an equation as said goal, wherein said subgoals include individual ones of said first plurality of numerals and equation elements, and wherein said goal sequence includes an equation sequence of said first plurality of numerals and equation elements and a second plurality of numerals and equation elements associated with said numerals wherein said equation is presented in said virtual environment and wherein said second plurality of numerals and equation elements includes said first plurality of numerals and equation elements with said second plurality of numerals and equation elements distributed in said virtual environment and wherein said goal includes a conformance selected from the group consisting of reproducing said equation in said equation sequence using said user frame of reference to select one or more of said second plurality of numerals and equation elements from said virtual environment, solving said equation by selecting, using said user frame of reference, one or more of said second plurality of numerals and equation elements, and combinations thereof.

2. An active learning method, the method comprising:

a) generating, using a kinetic interactive device, an activity interaction signal responsive to aerobically sustained large-muscle physical activity of a user operating said kinetic interactive device wherein said large-muscle physical activity results from sustained use of one or more large-muscles selected from the group consisting of arm large-muscle, leg large-muscle, shoulder large-muscle, and combinations thereof and wherein said activity interaction signal includes a motive element and a directional element;

b) generating, using said kinetic interactive device, a virtual environment on a display, said virtual environment supporting a virtual user frame-of-reference and including two or more virtual education elements and a goal for said virtual user frame of reference with respect to said virtual education elements wherein said virtual education elements are all independently-navigatable and concurrently presented in said virtual environment along with said goal and wherein said goal includes a plurality of independently navigatable subgoals arranged in a goal sequence;

c) producing, using said kinetic interactive device, an affected interaction of said virtual user frame of reference with said virtual education elements by navigating said user frame of reference within said virtual environment responsive to said motive element to control a speed of said virtual user frame of reference in said virtual environment and responsive to said directional element to control a direction of said virtual user frame of reference in said virtual environment responsive to said goal to select sequentially individual ones of said education elements in said goal sequence responsive to said subgoals;

d) measuring, using said kinetic interactive device, a conformation of said goal and said subgoals by said affected interaction; and e) producing, using said kinetic interactive device, feedback data of said virtual environment with said frame-of-reference in relation to said virtual education elements that provide said user with information regarding said goal and said conformation of said goal and said subgoals in said goal sequence by said affected interaction;

wherein said education elements include a first plurality numerals and equation elements and said goal includes an equation formed from said first plurality of numerals and equation elements, wherein individual numerals and equation elements of said equation form said subgoals and wherein said goal sequence includes an equation sequence of said subgoals forming said equation and wherein said education elements further include a second plurality of numerals and equation elements with said equation presented in said virtual environment and said second plurality of numerals and equation elements distributed in said virtual environment and wherein said producing step c) includes navigating said user frame of reference in said virtual environment to select individual ones of said second plurality of numerals and equation elements in said equation sequence responsive to said subgoals.

* * * * *